(12) United States Patent
Fukazawa et al.

(10) Patent No.: US 10,519,567 B2
(45) Date of Patent: Dec. 31, 2019

(54) BONDING METHOD OF CRYSTAL BODY

(71) Applicant: Japan Cell Co., Ltd., Machida-shi, Tokyo (JP)

(72) Inventors: Atsushi Fukazawa, Tokyo (JP); Satoshi Hayata, Tokyo (JP); Kazuyuki Sato, Tokyo (JP); Kiminori Omura, Tokyo (JP); Hiromu Kasai, Tokyo (JP)

(73) Assignee: JAPAN CELL CO., LTD., Machida-Shi (JP)

( * ) Notice: Subject to any disclaimer, the term of this patent is extended or adjusted under 35 U.S.C. 154(b) by 0 days.

(21) Appl. No.: 15/767,497

(22) PCT Filed: Mar. 8, 2017

(86) PCT No.: PCT/JP2017/009149
§ 371 (c)(1),
(2) Date: Apr. 11, 2018

(87) PCT Pub. No.: WO2017/154950
PCT Pub. Date: Sep. 14, 2017

(65) Prior Publication Data
US 2018/0298522 A1 Oct. 18, 2018

(30) Foreign Application Priority Data

Mar. 8, 2016 (JP) .................. 2016-043989
Feb. 16, 2017 (JP) .................. 2017-026513

(51) Int. Cl.
*B29C 65/00* (2006.01)
*C30B 29/20* (2006.01)
(Continued)

(52) U.S. Cl.
CPC .............. *C30B 29/20* (2013.01); *C30B 33/06* (2013.01); *B29C 65/18* (2013.01); *B29C 65/66* (2013.01);
(Continued)

(58) Field of Classification Search
CPC ......... C03B 29/08; C03B 29/12; B29C 65/18; B29C 65/66; B29C 66/004; B29C 66/342; B29C 66/345; B29C 66/45; B29C 66/70
(Continued)

(56) References Cited

U.S. PATENT DOCUMENTS 5,013,380 A * 5/1991 Aoshima ................. C30B 33/00
156/250
6,025,060 A * 2/2000 Meissner ................. C30B 33/00
428/220
(Continued)

FOREIGN PATENT DOCUMENTS

JP 3499717 12/2003
JP 4224336 11/2008
(Continued)

OTHER PUBLICATIONS

International Search Report, dated May 30, 2017 (May 30, 2017), 2 pages.

*Primary Examiner* — Mark A Osele
*Assistant Examiner* — Nickolas R Harm
(74) *Attorney, Agent, or Firm* — Rankin, Hill & Clark LLP

(57) ABSTRACT

To improve the production yield rate of a synthesis corundum cell superior in translucency, chemical resistance or an optical component comprising calcium fluoride. On the other end side of synthetic corundum piece, spacer intervenes between the surfaces which will be bonded. The spacer is crushed flat by pressure force which effects the other end side of synthetic corundum piece in the case of heat-treatment after the temporary bonding. Thereby, the spacer does not disturb the synthetic optical contacting or chemical pressurized fusion bonding state of corundum piece.

3 Claims, 4 Drawing Sheets

(51) Int. Cl.
　　　*C30B 33/06*　　　(2006.01)
　　　*B29C 65/18*　　　(2006.01)
　　　*C03B 29/12*　　　(2006.01)
　　　*C03B 29/08*　　　(2006.01)
　　　*B29C 65/66*　　　(2006.01)

(52) U.S. Cl.
　　　CPC .......... *B29C 66/004* (2013.01); *B29C 66/342* (2013.01); *B29C 66/345* (2013.01); *B29C 66/45* (2013.01); *B29C 66/70* (2013.01); *C03B 29/08* (2013.01); *C03B 29/12* (2013.01)

(58) Field of Classification Search
　　　USPC .............................. 156/297, 299, 308.2, 499
　　　See application file for complete search history.

(56) References Cited

U.S. PATENT DOCUMENTS

| | | | |
|---|---|---|---|
| 6,440,242 B1 * | 8/2002 | Fukazawa | C30B 29/20 156/89.11 |
| 10,052,848 B2 * | 8/2018 | Prest | B32B 9/002 |
| 2003/0016447 A1 * | 1/2003 | Kato | G02B 5/1814 359/569 |
| 2014/0071519 A1 * | 3/2014 | Chen | G02B 1/02 359/328 |
| 2014/0139978 A1 * | 5/2014 | Kwong | H04M 1/0202 361/679.01 |
| 2016/0362814 A1 * | 12/2016 | Uehara | C30B 29/12 |

FOREIGN PATENT DOCUMENTS

| | | |
|---|---|---|
| JP | 4251462 | 1/2009 |
| WO | 2015/098927 | 7/2015 |

\* cited by examiner

[FIG. 1]
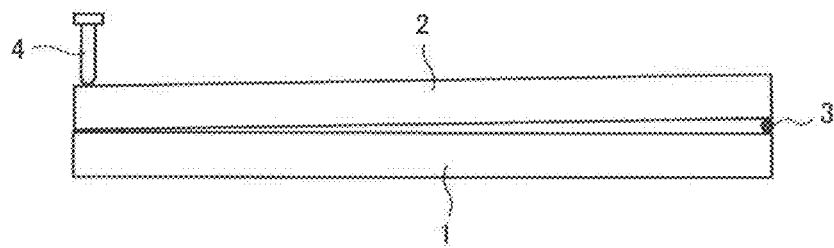
[FIG. 2]
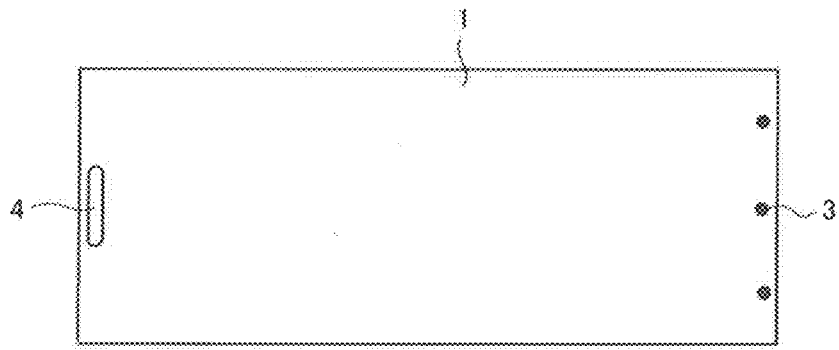
[FIG. 3]
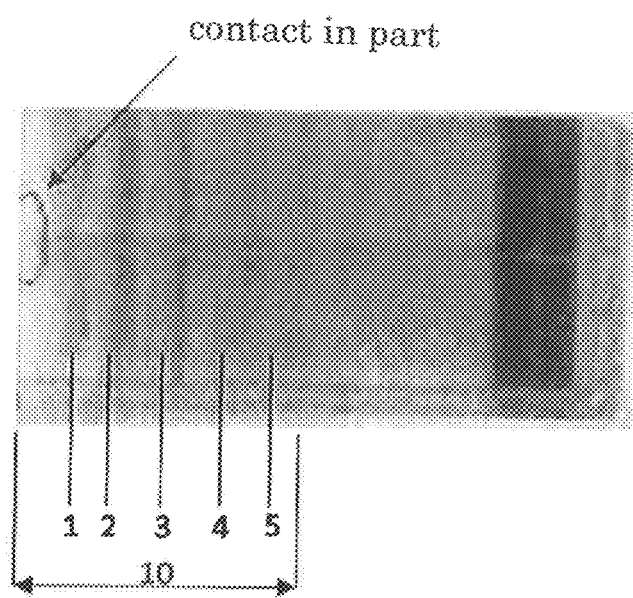

[FIG. 4]
(a)
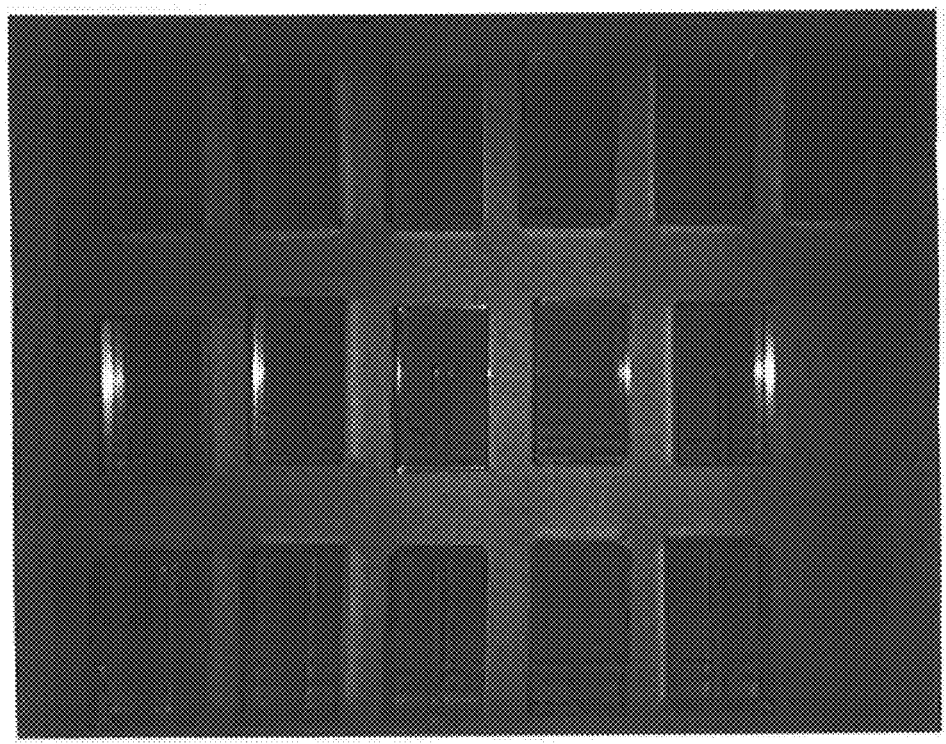
(b)
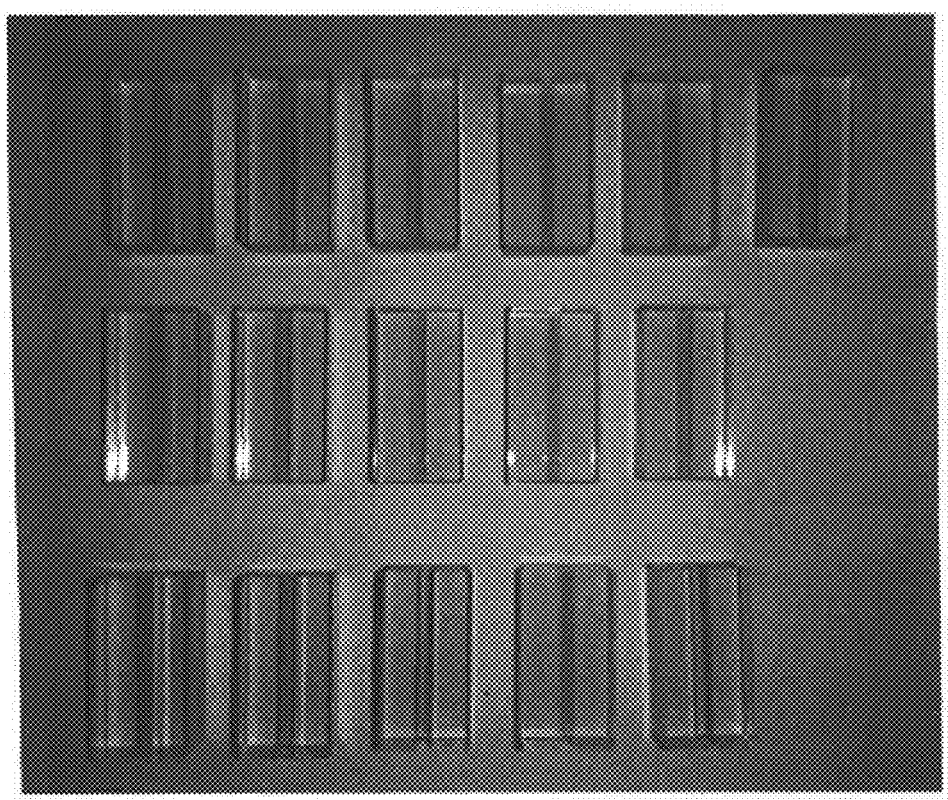

[FIG. 5]
(a)
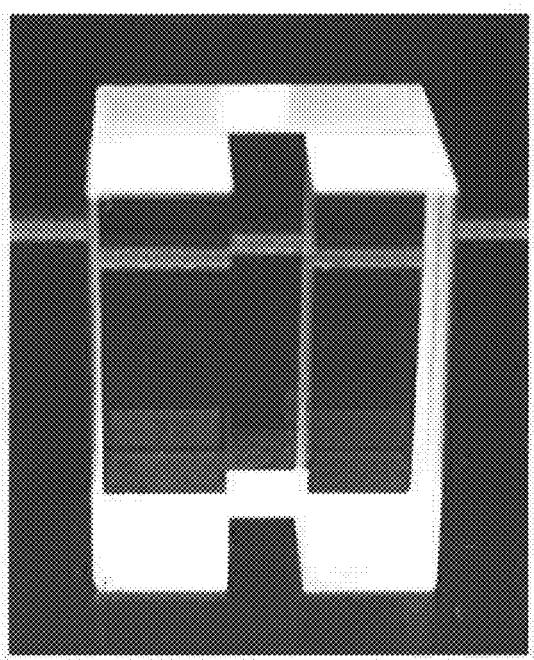
(b)
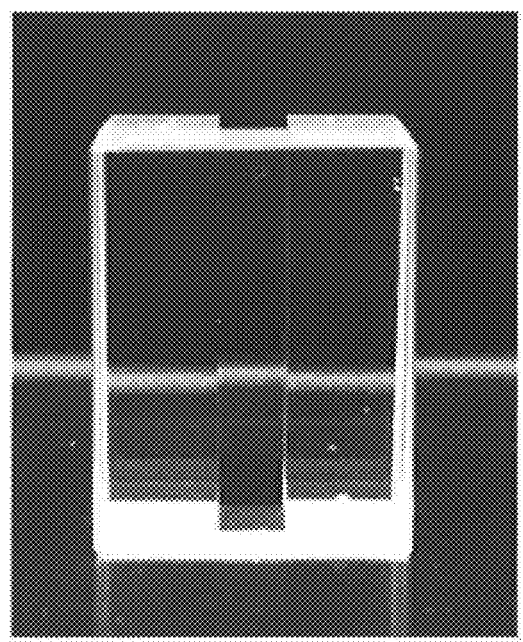

[FIG. 6]
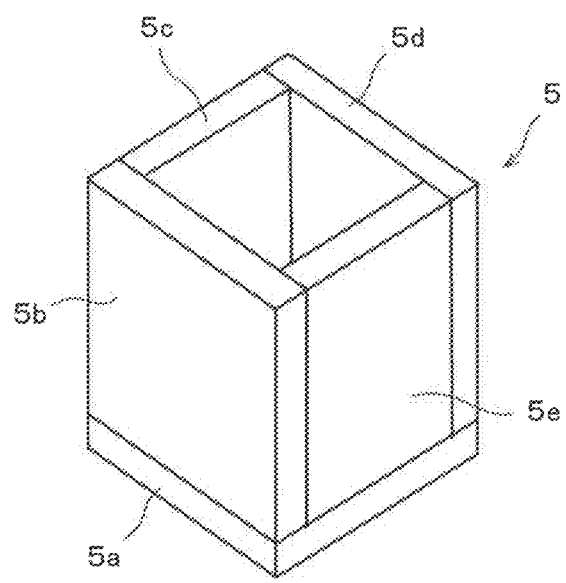

BONDING METHOD OF CRYSTAL BODY

FIELD OF THE INVENTION

The present invention relates to an bonding method of a crystal body such as synthetic corundum (Al2O3), calcium fluoride (CaF2) or magnesium fluoride (MgF2), synthetic corundum is used as the material of a flow-cell which is incorporated in a fine particle counter measuring fine particles included in liquids such as hydrogen fluoride, calcium fluoride (CaF2) and magnesium fluoride (MgF2) which are used as an optical component.

BACKGROUND ART

Conventionally, plural plate-shaped synthetic corundum pieces are prepared and these synthetic corundum pieces are bonded to manufacture a flow cell made by synthetic corundum.

Herein, when bond these by using an adhesive material, a boundary surface comes into existence in the bonding surface, then light refraction or light reflection occur, also, when make these thermal fusion, air bubbles confined in the bonding surface.

Therein, the applicant of this application suggested patent document 1-3.

The bonding method disclosed in the above patent document 1-3 is basically same, that is, at first cut off synthetic corundum pieces from a crystal block, polish the surface of each synthesis corundum piece, and overlap each polished surface, strongly press (pinch) the one end side of the two faced pieces of the synthetic corundum.

The press strength is assumed as interference fringe is inspected between surfaces of the synthetic corundum pieces, in this state, heat the two pieces of synthetic corundum at melting point (2,030 degrees Celsius) or less, then, it gradually assumes a fusion bonding state from one end of the synthetic corundum piece to the other end.

In the above, it becomes an optical contacting state or a chemical pressurized fusion bonding state in the strongly pressed one end side, the interference fringe disappears by heating, it is considered that the optical contacting state or the chemical pressurized fusion bonding state continues to the other end side by heating.

And, an optical boundary surface does not exist in the synthetic corundum body bonded together in this manner, then an extremely superior three-dimensional structure is provided.

PRIOR ART

Patent Document

[Patent Document 1] JP. PAT. No. 3499717
[Patent Document 2] JP. PAT. No. 4224336
[Patent Document 3] JP. PAT. No. 425146

DISCLOSURE OF INVENTION

Problems Solved by the Invention

The bonding structure which is manufactured by the method disclosed in patent document 1-3 is superior to chemical resistance and there is no malfunction such as the bonding surface peeling off, refraction or reflecting back the adhesion surface, On the other hand, there is a problem that the yield rate is insufficient.

In the conventional method, a gap is generated as interference fringes are made between the bonding surfaces by pressing one end side more strongly than the other end side, the other end side does not bind at all.

Thus, the gap formed between the bonding surfaces of the synthetic corundum pieces in the other end side is not constant.

This is regarded as the reason that the yield rate is insufficient.

The same problem occurs when crystal bodies such as calcium fluoride (CaF2) and magnesium fluoride (MgF2) are bonded together.

Means for Solving Problems

To solve the above described problem, an bonding method of the crystal body piece of the present invention is as follows.

Put the surfaces of the pieces of the crystal body such as synthetic corundum, calcium fluoride or magnesium fluoride which will be bonded together to face each other, strongly press the one end side of the two pieces of the crystal body pieces with the state of the overlap, generate an interference fringe-on the overlapped surfaces, dissipate the interference fringe on the overlapped surfaces by heating the crystal body pieces at a temperature less than melting point of the crystal body in this state, particularly, insert a minute spacer between the other end side of the crystal body pieces bonded together with each other, the minute spacer consists of material which can be crushed flat by the pressure force at the time of the heating.

As for the spacer, it does not interfere with the dissipation of the interference fringe by the heat-treatment.

That is, as for the spacer, it is necessary to have crush characteristics (elasticity, softness), as for the crush characteristics, the spacer does not interfere with the optical contact or chemical pressurized fusion bonding state.

An example of the spacer includes cotton fiber, but is not limited to this.

The diameter of the spacer depends on the bonding length of the synthetic corundum piece, 15-60 μm is preferably to generate interference fringes.

Also, in the bonding method of the present invention, with temporary bonding state pressing the one end of the crystal body piece to be bonded, it can be judged before heat-treatment whether a temporary bonding state is preferable or not by the number of the interference fringes per unit of crystal body piece length.

Also, the pressed part of the one end of the crystal body piece can be all or part of the widthwise direction.

Effects of the Invention

According to the present invention, when bonding crystal body pieces together by heat-treatment in the stare of pressing one end side more strongly than the other end side without the use of an adhesive material, the gap between the crystal body piece of the other end side can be precisely controlled by a spacer, thus, it can improve yield rate.

Also, with state of the temporary bonding before heat-treatment, whether the temporary bonding is good or bad can be judged by counting the number per unit length of an interference fringe formed on the bonding surfaces of a crystal body piece which will be bonded together.

Also, when pressure is applied by the jig in the widthwise direction, only a part of the widthwise piece is marked by the jig stick/arm limiting the incompatible portion after bonding and thereby saving on waste materials.

BRIEF DESCRIPTION OF THE DRAWINGS

FIG. 1 Side view of two overlapped synthetic corundum pieces.

FIG. 2 Top view of one piece of synthesis corundum pieces having a spacer on the end.

FIG. 3 Photograph of the interference fringe which comes when two synthetic corundum pieces are put on top of one another.

FIG. 4 (*a*) photograph of two synthetic corundum pieces before bonding, (*b*) photograph after bonding.

FIG. 5 (*a*) Front photograph of the structure when three magnesium fluoride crystal bodies are bonded simultaneously, (*b*) Rear photograph of the structure.

FIG. 6 Figure explains alternative embodiment.

BEST MODE FOR CARRYING OUT THE INVENTION

An embodiment of the present invention based on an attached drawing is explained below, alternatively in FIGS. 1-4, synthetic corundum is explained as crystallization in the illustrated embodiment.

FIG. 1 is a side view of two synthetic corundum pieces with the state of the overlap, FIG. 2 is a top view of one piece of synthesis corundum pieces having a spacer on the end, in accordance with the embodiment, at first prepare two synthetic corundum pieces 1, 2.

These synthetic corundum pieces 1, 2 are cut from a crystal block, the pieces are washed subsequently after having the surfaces which will be bonded together ground polish, and it is confirmed that there are no contamination and particles on the bonding surface.

Alternatively, while two synthetic corundum pieces are overlapped in the illustration example, but it synthetic corundum pieces are overlapped three or more can bond simultaneously.

It is not necessary to completely synchronize a crystal axis, edge and axial angle when overlapping the synthetic corundum piece 1, 2.

It is preferable to assume a displacement of less than 5 degrees of axes, edge and axial angle of the corundum piece 1, 2.

The one end of synthetic corundum piece 1,2 is pressed or clamped strongly by jig 4. It is possible to press the whole area of the widthwise direction by jig 4, however in the illustration example, it is pressed or clamped only at the center of the widthwise direction, thereby reducing incompatible portion after the bonding.

On the other end side of synthetic corundum piece 1, 2, spacer 3 intervenes between the surfaces which will be bonded.

The spacer 3 is larger than the fact to make plain with the figure, in the preferred embodiment, 30 µm diameter of cotton fiber is used.

Spacer 3 is crushed flat by pressure force which effects the other end side of synthetic corundum piece 1, 2 in the case of heat-treatment after the temporary bonding. Thereby, spacer 3 does not disturb the synthetic optical contacting or chemical pressurized fusion bonding state of corundum piece 1, 2.

As for spacer 3, gel beads can be applied too.

Material generating large quantities of gas in the case of heat-treatment after the temporary bonding are not recommendable suitable, because an air bubble may remain on the bonding surface.

FIG. 3 is a photograph of two synthetic corundum pieces overlapped and pressed on one end side, as is clear from this photograph, interference fringes are observed to come from the minute gap between surfaces which will be bonded.

The interval of the above described interference fringe is proportional to the size of the minute gap of the bonding surface, therefore, by counting the number of the interference fringes per unit length in the temporary bonding state, it is possible to judge beforehand whether the minute gap of the bonding surface of the synthetic corundum piece 1,2 is in the proper range or not. In this embodiment, 5 stripes are observed in a unit length.

The above-mentioned temporary bonding synthetic corundum piece is heated to a temperature less than the melting point of the corundum and maintained for a predetermined time.

Then, as for the one end, it already becomes optical contacting or chemical pressurized fusion bonding state, and this optical contacting or chemical pressurized fusion bonding state progresses from one end to the other end side, in accordance with this progress, existing gas is completely removed between the synthetic corundum pieces, then the whole bonding surface becomes optical contacting or chemical pressurized fusion bonding state.

FIG. 4(*a*) is a photograph of two synthetic corundum pieces before bonding, (*b*) is a photograph after bonding, in FIG. 4(*a*), 16 pairs of synthetic corundum pieces overlapped in vertical direction are observed.

In each pair, a flow channel to let a fluid go through is formed in the center portion.

A portion of both right and left side of this flow channel is an bonded surface, and an interference fringe is observed before heat-treatment.

Also photograph of (*b*) showing after heat-treatment, the above described interference fringe was not observed at all, and an optical boundary surface was not recognized in all specimens.

FIG. 5(*a*) is a front photograph of the structure bonded three magnesium fluoride crystal body simultaneously, (*b*) is a rear photograph of the structure, after the bonding, it is recognized that the above described interference fringes are not observed at all and optical boundary surface is not observed from these photographs.

FIG. 6 indicates a three-dimensional structure prepared by the present invention method.

The three-dimensional structure 5 consists of base plate 5*a* and four pieces of side-plates 5*b*, 5*c*, 5*d*, 5*e* comprising synthetic corundum, the side-plates are bonded along a sides of base plate 5*a*.

The three-dimensional structure 5 is manufactured by one heat-treatment by applying the present invention method to the facing portion between base plate 5*a* and side-plates 5*b*, 5*c*, 5*d*, 5*e*, and facing portion between each side-plate.

Also, the method of the present invention can be applied to the bonding of a crystal body such as calcium fluoride as well as synthetic corundum or magnesium fluoride.

In addition, the example is shown in which a synthetic corundum piece and synthetic corundum piece, or magnesium fluoride crystal body and magnesium fluoride crystal body were bonded, however, the present invention method can apply to the bonding of a synthetic corundum piece and magnesium fluoride crystal body piece, synthetic corundum piece and calcium fluoride crystal body piece, or magnesium fluoride crystal body piece and a calcium fluoride crystal body piece.

INDUSTRIAL APPLICABILITY

The method of the present invention can apply to not only flow cell installed in particle counter but also a lens, various optical components such as prisms, a machine part which requires hardness and a vacuum chamber where an bonding surface is a sealing up state.

As for the vacuum chamber, gas enclosure glass cell and high vacuum glass chamber are exemplified, which are used for e calibration of a variable wavelength laser, calibration of a light spectrum analyzer, calibration of a gas analyzer, calibration of a wavelength meter, frequency standard, stable frequency source, laser cooling of atoms in magneto optical trap method.

EXPLANATION OF LETTERS OR NUMERALS 1.2 . . . synthetic corundum piece, 3 . . . spacer, 4 . . . press jig, 5 . . . three-dimensional structure.

The invention claimed is:

1. A method of bonding crystal body pieces, the method comprising:
overlapping and contacting bonding surfaces of the crystal body pieces to define a first end side and a second end side of the crystal body pieces;
pressing the first end side of the crystal body pieces so as to generate an interference fringe between the bonding surfaces;
dissipating the interference fringe by heating the crystal body pieces to a temperature lower than a melting point of the crystal body pieces and inserting a spacer that intervenes between the bonding surfaces at the second end side of the crystal body pieces,
wherein the spacer consists of material which can be crushed flat by a pressure force at the time of heating, and
the crystal body pieces are synthetic corundum (Al2O3), calcium fluoride (CaF2), or magnesium fluoride (MgF2).

2. The method of bonding crystal body pieces according to claim 1, wherein the diameter of the spacer is 15-60 μm and the spacer comprises fiber.

3. The method of bonding crystal body pieces according to claim 1, wherein a pressing part pressed during the pressing of the first end side of the crystal body pieces is only a part of a widthwise direction of the crystal body pieces.

* * * * *